United States Patent [19]

Seebeck et al.

[11] 4,233,407
[45] Nov. 11, 1980

[54] APPARATUS FOR THE CONTINUOUS STERILE FERMENTATION

[75] Inventors: Dieter Seebeck, Wiesbaden; Jens A. Schildmann; Reinhard Weisrock, both of Nieder-Olm; Julius Koch, Eltville, all of Fed. Rep. of Germany

[73] Assignee: Peter Eckes, Nieder-Olm, Fed. Rep. of Germany

[21] Appl. No.: 960,893

[22] Filed: Nov. 15, 1978

Related U.S. Application Data

[63] Continuation of Ser. No. 738,404, Nov. 3, 1976, abandoned.

[51] Int. Cl.² .................. C12B 1/00; C12C 11/00; C12G 1/00
[52] U.S. Cl. .................................. 435/311; 99/276; 426/11; 426/15; 435/313; 435/316
[58] Field of Search ............... 426/11, 15, 16; 195/115, 109, 139, 142, 144; 435/290, 311, 313, 316; 99/276

[56] References Cited

U.S. PATENT DOCUMENTS

| | | | |
|---|---|---|---|
| 3,173,793 | 3/1965 | Shore et al. | 426/16 |
| 3,575,813 | 4/1971 | Rothmayr | 195/115 X |
| 4,009,286 | 2/1977 | Moll et al. | 195/115 X |

FOREIGN PATENT DOCUMENTS

274225  7/1927  United Kingdom.

OTHER PUBLICATIONS

Hind, H. L., Brewing Science and Practice, vol. II,- Chalmant & Hall Ltd., London, 1950, (pp. 796–803, 839 & 840).

Amerine et al., The Technology of Wine Making, 3rd Ed., The Avi Publ. Co., Inc. Westport, Conn. 1972, (pp. 262–264, 337, 338, 475–479).

*Primary Examiner*—David M. Naff
*Attorney, Agent, or Firm*—Sprung, Felfe, Horn, Lynch & Kramer

[57] ABSTRACT

Fermentation of solutions such as grape juice is carried out in an apparatus that permits continuously fermenting under sterile conditions. The apparatus is a closed slender upright hollow tower having connected thereto inlet and outlet means, sterile gas inlet means fitted with membrane filters, sintered candle means to introduce sterile gas, steam inlet means connected via sampling means for sterilizing with steam and pressure regulating means for maintaining excess pressure in the tower.

2 Claims, 1 Drawing Figure

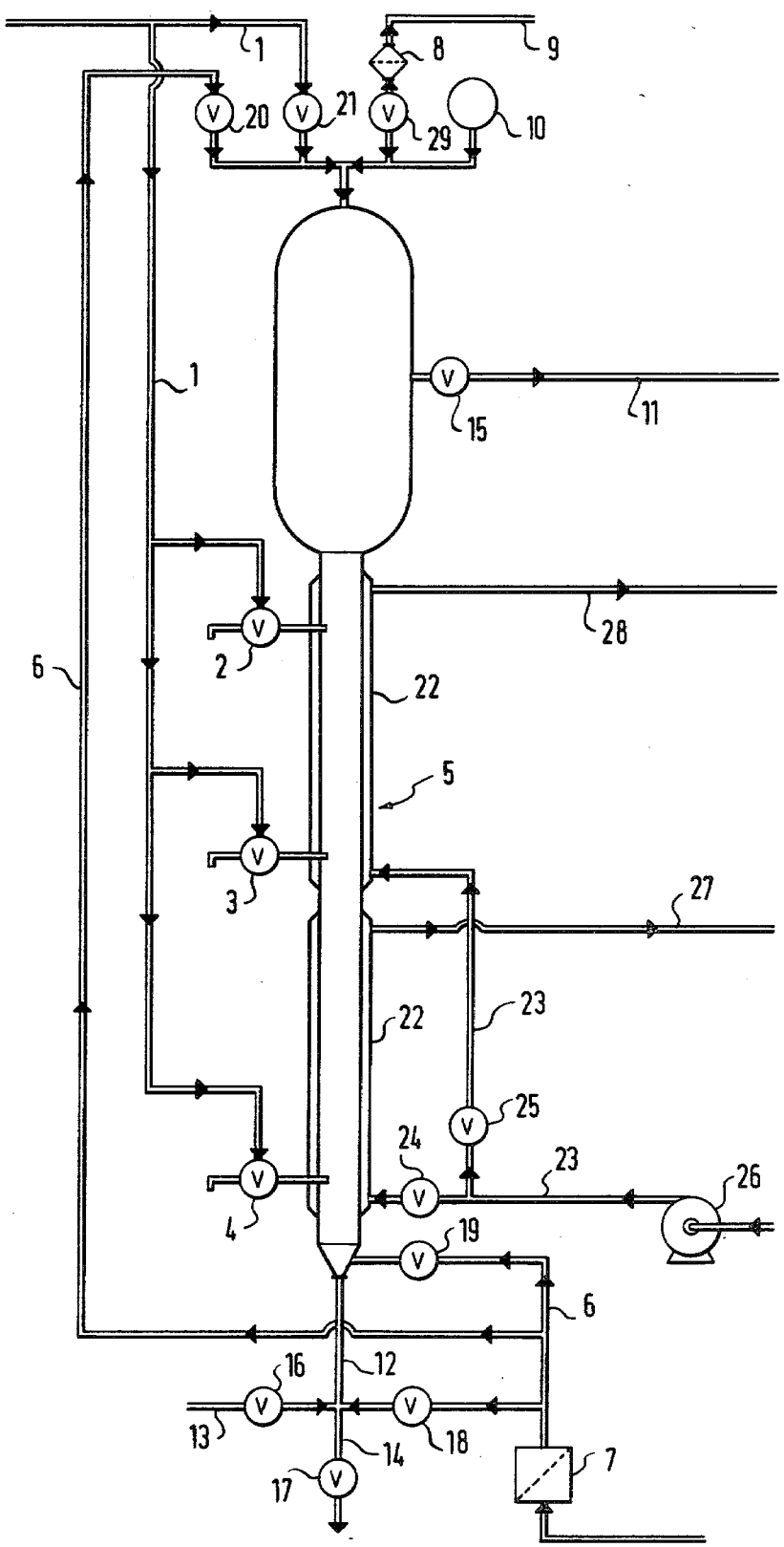

APPARATUS FOR THE CONTINUOUS STERILE FERMENTATION

This is a continuation of application Ser. No. 738,404, filed Nov. 3, 1976, now abandoned.

The invention relates to a process and apparatus for the continuous fermentation of solutions, especially of grape juice.

Devices are known in the brewing and wine industry for continuously fermenting beer wort or grape juice, in which the unfermented wort or the grape juice of the grape mash is fed continuously to a fermentation vat.

Furthermore, it is known from the Austrian Pat. No. 155,464, that the fermentation can be carried out in one or more double-chamber receptacles which are connected in series. For this purpose, the unfermented wort is fed to one of the chambers from below and, while air is blown in and the suspension is maintained, conveyed upwards, where it can flow over into the second chamber of the receptacle. When several double-chamber receptacles of this type are connected in series, the flow enters one of the chambers of the next receptacle from below, where it is carried upwards once again with the help of the air that is blown in. In every case, however, the last chamber is connected to a settling chamber, in which the fermented wort comes to rest and in whose lower region, adjacent the lower end of the double-chamber receptacle, the yeast can settle out. The lower region of the settling chamber is in open connection with the lower end of the or of each double-chamber receptacle, so that the yeast can again enter the double-chamber receptacle from below and, in so doing, the fermentation zone.

In addition, a device is known from the German Pat. No. 1,209,099, which comprises a hollow slender fermentation tower, which has inlets at its lower end for unfermented wort and for air and which is connected at its upper end over an overflow with a product-discharge line, which in turn is connected with a yeast settling chamber. The fermentation tower is connected at its upper end with a vent, through which carbon dioxide can escape. Finally, this fermentation tower can be equipped with facilities, which make it possible to recover the yeast which is carried along over the overflow in a yeast separator and to return it into the fermentation tower. In addition, distributed over its length and extending over its cross-section, the tower has perforated distribution elements, which ensure a uniform distribution of the yeast in the wort or the mash.

These previously known devices suffer from the common disadvantage that they represent a more or less open system, from which undesirable microorganisms, such as, for example, bacteria, cannot be entirely excluded, and thus changes may occur that could result in spoiling the contents of the fermentation device, so that the suitability and the efficiency of these devices leave much to be desired.

The present invention provides a process and apparatus by use of which sterile conditions are maintained, i.e., undesirable microorganisms from the air are excluded from the fermentation process. Essentially, the apparatus of the invention is based on a slender fermentation tower which has, at its lower end, inlets for the unfermented solution and for air and is, at its upper end, joined via an overflow to a product discharge line. Use of the apparatus makes it possible to ferment, e.g., a grape juice solution, to wine over a selected period of time, using a high concentration of yeast and excluding other microorganisms.

The apparatus of the invention is desirably fitted with a steam line connected with the fermentation tower, sampling valves, an air inlet for sterile air, membrane filters in the air inlet line and in the air exhaust line and a manometer for the static control of the sterilization process.

According to a preferred embodiment of the invention, the steam line is connected via the sampling valves and a further valve with the fermentation tower.

The invention is further illustrated by way of a preferred embodiment shown in the attached drawing.

With reference to the drawing, the inventive device comprises a fermentation tower 5, which is free of components in its interior or which, if necessary, can be provided with devices, for example, sintered candles, with the help of which gas, for example air, can be introduced. A line 1 is connected with the fermentation tower 5. Via line 1, steam (for example saturated steam) can be introduced into the fermentation tower via sampling valves 2, 3 and 4 or valve 21, for the purpose of sterilization. The fermentation tower 5 is provided at its lower end and at its upper side with an air intake 6, over which sterilized air is blown into the equipment. For this purpose, the air is intially passed over membrane filter 7, which retains the undesirable germs. In exhaust line 9, a further membrane filter 8 is provided, which enables the fermentation gases to leave, but prevents undesirable microorganisms and other impurities from entering. The membrane filters 7 and 8 are equipped with filter membranes, suitable for sterilizing air. The manometer 10 is used for statically monitoring the sterilization and fermentation processes and the device is operated in such a way that, especially while cooling the tower, no underpressure or vacuum arises, but there is instead at all times a slight overpressure in excess of atmospheric pressure in the equipment. Even after sterilization this overpressure is maintained, by introducing steam, from the time that the equipment has been cooled to room temperature until it is inoculated with yeast.

During operation, unfermented solution or freah grape juice is continuously introduced into the fermentation tower over line 13, valve 16 and line 12, in which solution or juice, after inoculation with yeast, the yeast is cultured and fermentation takes place, whereby, because of the continuous addition of fresh juice, the product flows off via the overflow (not shown), through valve 15 and into product discharge line 11. There is a certain calming of the yeast suspension in the enlarged, upper region of the fermentation tower 5, so that only a slight amount of yeast is drawn off with the product from the fermentation tower. Finally, the fermentation tower can be emptied over lines 12 and 13 as well as valve 17. The added air, sterilized with the help of membrane filter 17, can be introduced via valve 18 and line 12, via line 16 and valve 20 and via line 6 and valve 19.

Finally, the fermentation tower 5 is equipped with a heating and cooling mantle 22 (shown in two parts) that, via pump 26, supplies line 23 and valves 24 and 25 with the heating or cooling medium, that flows off over lines 27 and 28. With the help of this heating and cooling mantle, the fermentation tower is brought to the desired temperature and, during the fermentation, maintained at the optimum fermentation temperature.

To monitor the fermentation process, samples for checking the fermentation, the yeast, etc., can periodically be taken via sampling valves 2, 3 and 4 and analyzed. By automating the sampling and the analysis, it is also possible to control the fermentation process automatically.

Before and after taking samples, the sampling valves intended for this purpose are steamed in order to clean and sterilize them. Steam, introduced through line 1, is used for this purpose.

When starting up the operation of the inventive equipment, steam (saturated steam) is introduced into the equipment over line 1, whereby all valves are opened to such an extent that steam barely flows out of the equipment. At the same time, membrane filters 7 and 8 are also sterilized.

When the steaming is completed, sterilized air is blown into the fermentation tower 5 over line 6 and valves 19 and 20 or over line 6 and valve 18 and line 12. In so doing, the current of air is controlled with the help of the manometer 19 in such a way, that underpressure does not develop in the tower during cooling, but that instead a slight overpressure is maintained in the equipment. This overpressure is maintained even after the equipment has reached room temperature and while it is being inoculated.

Then, for culturing the yeast, unfermented nutrient solution is introduced into the fermenation tower 5 from below via line 13, valve 16 and line 12, whereby, if required for maintaining aerobic conditions, sterilized air is introduced into the equipment from below via line 6 and valve 19, which can advantageously be done with the help of sintered candles, which facilitate blowing fine bubbles of air into the fermentation tower. After the desired concentration of yeast has been attained in the fermentation tower, the fermentation process is continued continuously by constantly feeding in unfermented solution (via line 13, valve 16 and line 12) and constantly carrying away the products via valve 15 and line 11. The exhaust gases, formed during the culture, and also the carbon dioxide of the fermentation are conducted away via valve 29, the exhaust-gas line 9 and the membrane filter 8, so that a state is reached in which, though the exhaust gases escape, no harmful microorganisms can penetrate in from the external air.

Yeast cells which, together with the products, are removed from the fermentation tower via valve 15 and line 11, can be separated off and fed once again from below into the fermentation tower via line 13, valve 16 and line 12.

According to the invention, a process for fermenting solutions, especially grape juice, can be carried out continuously under sterile conditions in an extremely simple and advantageous manner, without having to fear that undesirable microorganisms will be carried in and so cause the fermenting material to be spoiled.

It will be understood that the specification and examples are illustrative but not limitative of the present invention and that other embodiments within the spirit and scope of the invention will suggest themselves to those skilled in the art.

What is claimed is:

1. Apparatus for continuously fermenting solutions under sterile conditions comprising a closed upright slender fermentation tower having a hollow interior, a lower end, and an enlarged upper end section, said lower end having connected thereto an inlet means for introducing unfermented feed solution into the lower end, a sterile gas inlet means fitted with a membrane filter and sintered candle means to bubble sterile gas into the lower end and a steam inlet means connected via a sampling means to sterilize the lower end and the sampling means by supplying steam thereto; said upper end section having connected thereto an outlet means for product discharge, a sterile gas inlet means fitted with a membrane filter to introduce sterile gas into the upper end section, a steam inlet means to sterilize the upper end section by supplying steam thereto, a gas exhaust outlet means fitted with a membrane filter and a pressure regulating means for maintaining excess pressure in the tower, and said tower having over its length, between the lower end and upper end section, a plurality of steam inlet means connected via a sampling means for supplying steam to sterilize the length of the tower between the lower end and upper end sections and to sterilize the sampling means.

2. Apparatus as claimed in claim 1 wherein said sterile gas inlet means is for introducing sterile air.

* * * * *